US010221434B2

(12) United States Patent
Seo et al.

(10) Patent No.: US 10,221,434 B2
(45) Date of Patent: Mar. 5, 2019

(54) MICROORGANISMS FOR PRODUCTION OF O-SUCCINYL HOMOSERINE AND METHOD FOR PRODUCTION OF O-SUCCINYL HOMOSERINE USING THE SAME

(71) Applicant: CJ CHEILJEDANG CORPORATION, Seoul (KR)

(72) Inventors: Chang Il Seo, Incheon (KR); So Young Kim, Gyeonggi-do (KR); Yong Uk Shin, Gyeonggi-do (KR); Kwang Ho Na, Seoul (KR); Hye Won Um, Gyeonggi-do (KR); In Kyung Heo, Seoul (KR)

(73) Assignee: CJ CHEILJEDANG CORPORATION, Seoul (KR)

( * ) Notice: Subject to any disclaimer, the term of this patent is extended or adjusted under 35 U.S.C. 154(b) by 131 days.

(21) Appl. No.: 15/031,707

(22) PCT Filed: Oct. 22, 2014

(86) PCT No.: PCT/KR2014/009970
§ 371 (c)(1),
(2) Date: Apr. 22, 2016

(87) PCT Pub. No.: WO2015/060649
PCT Pub. Date: Apr. 30, 2015

(65) Prior Publication Data
US 2016/0304920 A1 Oct. 20, 2016

(30) Foreign Application Priority Data
Oct. 23, 2013 (KR) .................. 10-2013-0126602

(51) Int. Cl.
*C12P 13/06* (2006.01)
*C12N 9/10* (2006.01)
(52) U.S. Cl.
CPC ............ *C12P 13/06* (2013.01); *C12N 9/1029* (2013.01); *C12Y 203/01046* (2013.01)
(58) Field of Classification Search
None
See application file for complete search history.

(56) References Cited

U.S. PATENT DOCUMENTS

| 7,851,180 | B2 | 12/2010 | Shin et al. | |
|---|---|---|---|---|
| 2010/0184164 | A1* | 7/2010 | Kim | C12N 9/1029 435/113 |
| 2011/0053253 | A1* | 3/2011 | Kim | C12N 9/0006 435/252.33 |

FOREIGN PATENT DOCUMENTS

| JP | 2012-213401 A | 11/2012 |
|---|---|---|
| KR | 10-0620092 B1 | 8/2006 |
| KR | 10-0905381 B1 | 6/2009 |
| KR | 10-2009-0106365 A | 10/2009 |
| WO | 2005075625 A1 | 8/2005 |
| WO | 2008127240 A1 | 10/2008 |
| WO | 2012/087039 A2 | 6/2012 |

OTHER PUBLICATIONS

Schumann et al., "Fructose-6-phosphate Aldolase Is a Novel Class I Aldolase from *Escherichia coli* and Is Related to a Novel Group of Bacterial Transaldolases", JBC, 2001, 276(14):11055-11061.*
Zinger-Yosovich et al., "Production and properties of the native Chromobacterium violaceum fucose-binding lectin (CV-IIL) compared to homologous lectins of Pseudomonas aeruginosa (PA-IIL) and Ralstonia", Microbiology (2006), 152, 457-463. DOI 10.1099/mic.0.28500-0.*
Brenda Information on EC 2.3.1.31—homoserine O-acetyltransferase. Retrieved from < https://www.brenda-enzymes.org/enzyme.php?ecno=2.3.1.31 > on Mar. 20, 2018.*
Datsenko and Wanner, "One-step inactivation of chromosomal genes in *Escherichia coli* K-12 using PCR products," PNAS 97(12): 6640-6645, Jun. 6, 2000.
NCBI Reference Sequence: WP_011134341, "homoserine O-acetyltransferase [Chromobacterium violaceum]," Mar. 4, 2015.
Posfai et al., "Versatile Insertion Plasmids for Targeted Genome Manipulations in Bacteria: Isolation, Deletion, and Rescue of the Pathogenicity Island LEE of the *Escherichia coli* O157:H7 Genome," Journal of Bacteriology 179(13): 4426-4428, Jul. 1997.
Database UniProtKB/Swiss-Prot, "Full Homoserine O-acetyltransferase; EC-2.3.1.31; Chromobacterium violaceum (strain ATCC 12472 / DSM 30191 / JCM 1249 / NBRC 12614 / NCIMB 9131 / NCTC 9757)," Database Accession No. Q7NZY3, Mar. 15, 2005, two pages.
Database EMBL-EBI, "Chromobacterium violaceum ATCC 12472 probable homoserine O-acetyltransferase," Database Accession No. AAQ58462, Apr. 7, 2010, three pages.

* cited by examiner

*Primary Examiner* — Suzanne M Noakes
(74) *Attorney, Agent, or Firm* — Cooley LLP

(57) ABSTRACT

The present invention relates to a polypeptide which is resistant to feedback inhibition by methionine and has an activity of homoserine O-succinyltransferase, a microorganism for producing O-succinylhomoserine which expresses the polypeptide, and a method for producing O-succinylhomoserine using the same.

10 Claims, No Drawings
Specification includes a Sequence Listing.

MICROORGANISMS FOR PRODUCTION OF O-SUCCINYL HOMOSERINE AND METHOD FOR PRODUCTION OF O-SUCCINYL HOMOSERINE USING THE SAME

CROSS-REFERENCES TO RELATED APPLICATIONS

This application is a U.S. national phase application of International PCT Patent Application No. PCT/KR2014/009970, which was filed on Oct. 22, 2014, which claims priority to Korean Patent Application No. 10-2013-0126602, filed Oct. 23, 2013. These applications are incorporated herein by reference in their entireties.

STATEMENT REGARDING SEQUENCE LISTING

The Sequence Listing associated with this application is provided in text format in lieu of a paper copy, and is hereby incorporated by reference into the specification. The name of the text file containing the Sequence Listing is HANO_046_00US_SeqList_ST25.txt. The text file is 12 KB, was created on Apr. 22, 2016, and is being submitted electronically via EFS-Web.

TECHNICAL FIELD

The present invention relates to an isolated polypeptide which has a resistance to feedback inhibition by methionine and a homoserine O-succinyltransferase activity, a microorganism expressing the polypeptide, and a method for producing O-succinylhomoserine using the same.

BACKGROUND ART

Most microorganisms present in nature are known to utilize O-succinylhomoserine or O-acetylhomoserine as an intermediate for the biosynthesis of methionine. Generally, O-succinylhomoserine is produced by homoserine O-succinyltransferase (MetA) which conjugates the succinyl group of succinyl-coA to homoserine, and O-acetylhomoserine is produced by homoserine O-acetyltransferase (MetX) which conjugates acetyl group of acetyl-coA to homoserine. That is, in producing O-succinylhomoserine among intermediates, metA is one of the most important genes in the development of microorganisms producing the same. Meanwhile, unlike MetA, MetX is known to be not feedback inhibited and have high enzyme stability.

O-succinylhomoserine can be produced using a strain with a deletion of metB gene encoding cystathionine gamma synthase in the methionine biosynthesis pathway. However, the O-succinylhomoserine-producing strain requires L-methionine. For this reason, the activity of homoserine O-succinyltransferase is inhibited by being subjected to feedback inhibition by the methionine added to the medium, and eventually, O-succinylhomoserine cannot be obtained at high concentration.

Accordingly, many prior patents have focused their studies on the release of feedback inhibition of metA from a feedback control system. However, the homoserine O-succinyltransferase encoded by metA has problems in that the wild type protein itself has low stability and that the introduction of a mutation for the release of feedback inhibition aggravates the instability. Accordingly, for the development of an O-succinylhomoserine-producing strain with high productivity, it is necessary that the feedback inhibition of the metA gene be removed and the enzyme stability be secured.

DISCLOSURE

Technical Problem

In order to solve the phenomenon of feedback inhibition of metA and the enzyme instability problem described above, the present inventors have endeavored to develop a homoserine O-succinyltransferase, which has secured enzyme stability while not being feedback inhibited by methionine, and in this regard, screened novel enzymes having the activity. As a result of selecting the thus-screened candidate genes and culturing in a flask after introducing them into *Escherichia* sp., the present inventors have discovered the production of O-succinylhomoserine, and that the thus-selected genes have a homoserine O-succinyltransferase activity and a resistance to feedback inhibition by methionine, thereby completing the present invention.

Technical Solution

An object of the present invention is to provide a novel isolated polypeptide having a resistance to the feedback inhibition by methionine and a homoserine O-succinyltransferase activity.

Another object of the present invention is to provide a polynucleotide encoding the novel isolated polypeptide.

A further object of the present invention is to provide a microorganism for producing O-succinylhomoserine, which expresses the novel isolated polypeptide.

A further object of the present invention is to provide a method for producing O-succinylhomoserine using the above microorganism.

Advantageous Effects of the Invention

The microorganism for producing O-succinylhomoserine including a novel isolated polypeptide, which has a resistance to the feedback inhibition by methionine and a homoserine O-succinyltransferase activity, can have a resistance to the feedback inhibition by methionine and produce O-succinylhomoserine with high yield, and thus can be effectively used for the production of L-methionine, which uses the same as the precursor, with high yield.

BEST MODE FOR CARRYING OUT THE INVENTION

In order to achieve the above objects, in an aspect, the present invention provides a novel isolated polypeptide having a resistance to feedback inhibition by methionine and a homoserine O-succinyltransferase activity.

As used herein, the term "homoserine O-succinyltransferase activity" refers to the activity of converting homoserine into O-succinylhomoserine during methionine biosynthesis.

As used herein, the term "feedback inhibition" refers to the inhibition of the activity of homoserine O-succinyltransferase by methionine during methionine biosynthesis.

The polypeptide of the present invention is characterized in that it has an amino acid sequence of SEQ ID NO: 29 having the homoserine O-succinyltransferase activity, and a resistance to feedback inhibition by methionine. Any polypeptide that shares a sequence homology of 80% or greater, specifically 90% or greater, more specifically 95% or greater, and even more specifically 97% or greater with the above polypeptide is also within the scope of the present invention, insofar as the polypeptide has the homoserine O-succinyltransferase activity and the resistance to the feedback inhibition by methionine suggested in the present invention. The homology may be determined using BLAST, which is a reference algorithm, or FASTA by Pearson [Methods Enzymol.,183, 63(1990), infra]. Based on the BLAST algorithm, programs called BLASTN and BLASTX have been developed [at the world wide web address: ncbi.nlm.nih.gov ].

In another aspect, the present invention provides an isolated polynucleotide encoding the above polypeptide. Specifically, the polypeptide may be encoded by the polynucleotide sequence of SEQ ID NO: 36, due to codon degeneracy, those polynucleotides which have a sequence homology of at least 80% to the above sequence, specifically 90% or greater, more specifically 95% or greater, and even more specifically 97% or greater are also within the scope of the present invention, although not limited thereto.

In still another aspect, the present invention provides a vector which includes the polynucleotide in an operable manner.

As used herein, the term "vector" refers to a DNA construct including the nucleotide sequence of the polynucleotide encoding a protein of interest, in which the protein of interest is operably linked to a suitable regulatory sequence so that the protein of interest can be expressed in an appropriate host. The regulatory sequence may include a promoter capable of initiating transcription, any operator sequence for the regulation of the transcription, a sequence encoding an appropriate mRNA ribosome-binding domain, and a sequence regulating the termination of transcription and translation. The vector, after being transformed into an appropriate host, may be replicated or function irrespective of the host genome, or may be integrated into the host genome itself.

The vector used in the present invention may not be particularly limited as long as the vector is replicable in the host, and any vector known in the art may be used.

In still another aspect, the present invention provides an O-succinylhomoserine producing microorganism expressing a polypeptide, having a resistance to feedback inhibition by methionine and a homoserine O-succinyltransferase activity.

As used herein, the term "an O-succinylhomoserine producing microorganism" may refer to a microorganism which can produce O-succinylhomoserine and store it intracellularly and extracellularly.

The microorganism for producing O-succinylhomoserine includes prokaryotic- and eukaryotic microorganism strains, e.g., the microorganism strains belonging to the genus *Escherichia*, the genus *Erwinia*, the genus *Serratia*, the genus *Providencia*, the genus *Corynebacterium* and the genus *Brevibacterium*, but not limited thereto. Specifically, the microorganism may be a microorganism belonging to the genus *Escherichia*, for example, *Escherichia coli*.

The O-succinylhomoserine producing microorganism may be prepared using microorganism strains which produce L-lysine, L-threonine, or L-isoleucine, and specifically, using an L-threonine producing strain. Since the L-threonine producing strain is a strain capable of synthesizing L-threonine and homoserine as a precursor of O-succinylhomoserine, a large amount of methionine precursors, i.e., O-succinylhomoserine, can be synthesized using the strain.

In the present invention, the expression of the polypeptide may be achieved by transforming with a recombinant vector which includes a gene encoding the polypeptide in an operable manner or by inserting a polynucleotide encoding the polypeptide into the chromosome, but the methods are not limited thereto.

As used herein, the term "transformation" refers to a process of introducing a vector including a polynucleotide encoding a target protein into a host cell, thereby enabling the expression of the polynucleotide encoded by the protein in the host cell. For the transformed polynucleotide, it does not matter whether it is inserted into the chromosome of a host cell and located therein or located outside the chromosome, as long as it can be expressed in the host cell. The polynucleotide may be inserted in any form insofar as it can be introduced into a host cell and expressed therein. For example, the polynucleotide may be introduced into a host cell in the form of an expression cassette, which is a polynucleotide construct including all essential elements required for self-expression. The expression cassette may conventionally include a promoter operably connected to the open reading frame ("ORF", hereinafter) of the gene, a transcription termination signal, a ribosome-binding domain, and a translation termination signal. The promoter used in the present invention may not be particularly limited as long as it can initiate the transcription of the polynucleotide encoding the target protein in a host cell with high frequency, and any promoter known in the art may be used. Specifically, T7 promoter, trc promoter, tac promoter, CJ1 promoter (Korean Pat. No. 0620092), etc., may be used.

In an exemplary embodiment of the present invention, the metB gene encoding cystathionine gamma synthase in the microorganism may be further deleted or weakened.

In an exemplary embodiment of the present invention, the thrB gene encoding homoserine kinase and the metA gene encoding homoserine O-succinyltransferase in the microorganism may be further deleted or weakened.

Additionally, in an exemplary embodiment, the microorganism may be an *Escherichia* sp., in which phosphoenolpyruvate carboxylase, aspartate aminotransferase, and aspartate-semialdehyde dehydrogenase are further enhanced.

In the present invention, the sequences of the genes can be obtained from databases such as The National Center for Biotechnology Information (NCBI).

As used herein, the term "deletion" refers to a type of removal, within the chromosome, of a part or the entirety of a nucleotide sequence region of a target gene from the nucleotide sequence corresponding to the initiation codon to that of the termination codon, or a part or the entirety of the nucleotide sequence region of a regulatory region thereof.

As used herein, the term "weakening" refers to removal or reduction of intracellular activity of at least one enzyme being encoded by the corresponding polynucleotide in a microorganism strain. For example, the expression of a protein may be weakened by modifying the expression regulatory sequence or the nucleotide sequence of 5'-UTR of a gene, or the activity of a protein may be weakened by substituting the initiation codon or introducing a mutation in the ORF region of the corresponding gene.

As used herein, the term "enhancing" refers to an increase of intracellular activity of an enzyme being coded by the corresponding polynucleotide. The enhancement of the intracellular activity of an enzyme may be achieved by overexpression of a gene or by the introduction of a modification of the polynucleotide sequence itself.

The overexpression of the polynucleotide may be a modification by a substitution of the expression regulatory sequence or a modification by a mutation, a substitution of the initiation codon, an additional insertion of the polynucleotide into the chromosome or an increase of copy number by an introduction using a vector, or a combination thereof.

The expression regulatory sequence is a sequence controlling the expression of the polynucleotide, which is operably connected thereto, e.g., a promoter, a terminator, an enhancer, a silencer, a Shine-Dalgarno sequence, etc. The initiation codon consisting of TTG or GTG may be substituted with ATG to increase the enzyme activity of the corresponding gene or decrease the enzyme activity of the corresponding gene by substituting in the opposite way. The polynucleotide may be one with an increased copy number by being inserted into a particular site within the chromosome. The particular site may include, for example, a transposon or an intergenic region. Additionally, the polynucleotide may be that which was inserted into an expression vector, which was again introduced into a host cell, thereby having an increased copy number.

In another aspect, the present invention provides a method for producing O-succinylhomoserine including culturing the above microorganism in a medium to produce O-succinylhomoserine, and obtaining the O-succinylhomoserine from the microorganism or the medium.

The culturing of the microorganism strain for producing the O-succinylhomoserine prepared above may be performed according to the appropriate medium and conditions for culture known in the art. The culture process may be easily adjusted for use by one of ordinary skill in the art according to the strain to be selected. Specifically, the culture may be a batch culture, a continuous culture, and a fetch culture, but is not limited thereto. These various culture processes are disclosed, for example, in a reference ("*Biochemical Engineering*" by James M. Lee, Prentice-Hall International Editions, pp 138-176).

The media used for culture must appropriately meet the requirements for particular strains. Examples of the media for various microorganisms are disclosed, for example, in a reference ("*Manual of Methods for General Bacteriology*" by the American Society for Bacteriology, Washington D.C., USA, 1981). The media can include various carbon sources, nitrogen sources, and trace elements. Examples of the carbon source to be contained in the media may include carbohydrates such as glucose, sucrose, lactose, fructose, maltose, starch, and cellulose; fats such as soybean oil, sunflower oil, castor oil, and coconut oil; fatty acids such as palmitic acid, stearic acid, and linoleic acid; alcohols such as glycerol and ethanol; and organic acids such as acetic acid. These carbon sources may be used alone or in combination. Examples of the nitrogen source to be contained in the media may include organic nitrogen sources such as peptone, yeast extract, meat gravy, malt extract, corn steep liquor (CSL), and bean flour; and inorganic nitrogen sources such as urea, ammonium sulfate, ammonium chloride, ammonium phosphate, ammonium carbonate, and ammonium nitrate. These nitrogen sources may be used alone or in combination. As a phosphorous source, the media may include potassium dihydrogen phosphate, dipotassium hydrogen phosphate, and corresponding sodium-containing salts. Additionally, the culture media may include metals such as magnesium sulfate and iron sulfate. Furthermore, amino acids, vitamins, and appropriate precursors, etc., may be included. These culture media or precursors may be added to the culture in the form of a batch culture or continuous culture.

Additionally, the pH of the culture may be adjusted by adding a compound such as ammonium hydroxide, potassium hydroxide, ammonia, phosphoric acid, and sulfuric acid during cultivation in an appropriate manner. Additionally, bubble formation may be prevented during the cultivation using an antifoaming agent such as fatty acid polyglycol ester. Additionally, an oxygen gas or a gas containing an oxygen gas (e.g., air) may be added to a culture to maintain aerobic conditions in the culture. The culture temperature may be in the range from 20° C. to 45° C., and specifically from 25° C. to 40° C. The cultivation may be continued until the desired amount of O-succinylhomoserine product is obtained, and specifically for from 10 hours to 160 hours.

The O-succinylhomoserine produced by the method of the present invention may be converted into methionine by cystathionine gamma synthase or O-succinylhomoserine sulfhydrylase. Additionally, succinic acid may be obtained as a byproduct in addition to L-methionine, by reacting the O-succinyl-L-homoserine produced by the method of the present invention with $CH_3SH$.

In still another aspect, the present invention relates to the use of a polypeptide having a resistance to feedback inhibition by methionine and a homoserine O-succinyltransferase activity, in which the polypeptide has an amino acid sequence of SEQ ID NO: 29. The novel isolated polypeptide of the present invention was confirmed to have a resistance to feedback inhibition by methionine and to be able to produce O-succinylhomoserine with high yield, and thus the polypeptide can be used for producing O-succinylhomoserine.

DETAILED DESCRIPTION OF THE INVENTION

Hereinafter, the present invention will be described in more detail with reference to the following Examples. However, these Examples are for illustrative purposes only, and the invention is not intended to be limited by these Examples.

EXAMPLE 1

Preparation of Threonine-Producing Strain Based Parent Strain (1) Deletion of metB Gene For the characterization of substrate specificity and activity of metX gene, a strain which can accumulate homoserine and has a deletion in utilization of acyl homoserine. The strain was constructed based on the FTR2533 (KCCM 10541), a threonine-producing strain disclosed in International Patent Publication No. WO 05/075625.

The metB gene encoding cystathionine synthase in a threonine-producing strain, the FTR2533 (KCCM 10541) strain, was deleted by the FRT-one-step PCR deletion method (PNAS (2000) vol 97: P 6640-6645). A deletion cassette was constructed by PCR using the primers of SEQ ID NO: 1 and SEQ ID NO: 2, and the pKD3 vector (PNAS (2000) vol 97: P 6640-6645) as a template. The PCR was performed for 30 cycles under the following conditions: denaturation at 94° C. for 30 s, annealing at 55° C. for 30 s, and polymerization at 72° C. for 1 m.

```
                                           <SEQ ID NO: 1>
    5' ttactctggt gcctgacatt tcaccgacaa agcccaggga
       acttcatcac gtgtaggctg gagctgcttc 3'

<SEQ ID NO: 2>
    5' ttaccccttg tttgcagccc ggaagccatt ttccaggtcg
       gcaattaaat catatgaata tcctccttag 3'
```

The resulting PCR product was electrophoresed in a 1.0% agarose gel and the 1.2 kbp DNA band obtained therefrom was purified. The recovered DNA fragment was electroporated into the FTR2533 strain, which was already transformed with the pKD46 vector (PNAS (2000) vol 97: P6640-6645).

For the electroporation, the FTR2533 strain transformed with the pKD46 vector was cultured in LB medium containing 100 μg/L ampicillin and 5 mM L-arabinose at 30° C. until OD600 reached 0.6. The resultant was washed twice with sterile distilled water and then washed once with 10% glycerol for use. The electroporation was performed at 2500V.

The recovered strain was plated on LB plate medium containing 25 μg/L chloramphenicol, cultured at 37° C. overnight, and the strain showing resistance to chloramphenicol was selected. The selected strain was subjected to PCR using the same primers while using the strain as a template, and the deletion of metB gene was confirmed by observing the presence of a 1.2 kb band of the gene in a 1.0% agarose gel. The thus-confirmed strain was transformed again with the pCP20 vector (PNAS (2000) vol 97: P6640-6645) and cultured in LB medium, and again the final strain with a deletion of metB gene having a reduced size of 150 bp, which was confirmed in a 1.0% agarose gel, was constructed by performing PCR under the same conditions and confirmed that the chloramphenicol marker was removed from the strain. The thus-constructed strain was named as "CJMA1".

(2) Deletion of thrB Gene

The thrB gene encoding homoserine kinase was deleted in the thus-constructed CJMA1 strain using the FRT-one-step PCR deletion method, as in the case of metB gene deletion.

A thrB deletion cassette was constructed by PCR using the primers of SEQ ID NO: 3 and SEQ ID NO: 4, and the pKD4 vector (PNAS (2000) vol 97: P 6640-6645) as a template. The PCR was performed for 30 cycles under the following conditions: denaturation at 94° C. for 30 s, annealing at 55° C. for 30 s, and extension at 72° C. for 1 m.

```
                                            <SEQ ID NO: 3>
    aaagaatatg ccgatcggtt cgggcttagg ctccagtgcc
    tgttcggtgg gtgtaggctg gagctgcttc <SEQ ID NO: 4>
    agacaaccga catcgctttc aacattggcg accggagccg
    ggaaggcaaa catatgaata tcctccttag
```

The resulting PCR product was electrophoresed in a 1.0% agarose gel and the 1.6 kbp DNA band obtained therefrom was purified. The recovered DNA fragment was electroporated into the CJMA1 strain, which was already transformed with the pKD46. The recovered strain was plated on LB plate medium containing 50 μg/L kanamycin, cultured at 37° C. overnight, and the strain showing resistance to kanamycin was selected. The selected strain was subjected to PCR under the same conditions using the primers of SEQ ID NOS: 3 and 4, and the deletion of thrB gene was confirmed by observing the presence of a 1.6 kb band of the gene in a 1.0% agarose gel. The thus-confirmed strain was transformed again with the pCP20 vector and cultured in LB medium, and the final strain with a deletion of thrB gene having a reduced size of 150 bp, which was confirmed in a 1.0% agarose gel, was constructed by performing PCR under the same conditions and confirmed that the kanamycin marker was removed from the strain. The thus-constructed strain was named as "CJMA2".

(3) Deletion of metA Gene

For the characterization of substrate specificity and activity of the metX gene derived from *Chromobacterium Violaceum* in the CJMA2 strain, the original metA gene on the chromosome was deleted based on the CJMA2 strain, in which metB and thrB genes are deleted, in the FTR2533 (KCCM 10541) strain. The metA gene was deleted by the FRT-one-step PCR deletion method.

A metA deletion cassette was constructed by PCR using the primers of SEQ ID NOS: 5 and 6, and the pKD3 vector (PNAS (2000) vol 97: P6640-6645) as a template. The PCR was performed for 30 cycles under the following conditions: denaturation at 94° C. for 30 s, annealing at 55° C. for 30 s, and extension at 72° C. for 1 m.

```
                                            <SEQ ID NO: 5>
    caatttcttg cgtgaagaaa acgtctttgt gatgacaact
    tctcgtgcgt gtgtaggctg gagctgcttc <SEQ ID NO: 6>
    aatccagcgt tggattcatg tgccgtagat cgtatggcgt
    gatctggtag catatgaata tcctccttag
```

The resulting PCR product was electrophoresed in a 1.0% agarose gel and the 1.2 kbp DNA band obtained therefrom was purified. The recovered DNA fragment was electroporated into the CJMA2 strain, which was already transformed with the pKD46. The recovered strain was plated on LB plate medium containing chloramphenicol, cultured at 37° C. overnight, and the strain showing resistance to chloramphenicol was selected.

The selected strain was subjected to PCR under the same conditions using the primers of SEQ ID NOS: 5 and 6, and the deletion of metA gene was confirmed by observing the presence of a 1.1 kb band of the gene in a 1.0% agarose gel. The thus-confirmed strain was transformed again with the pCP20 vector and cultured in LB medium, and the final strain with a deletion of thrB gene having a reduced size of 100 bp, which was confirmed in a 1.0% agarose gel, was constructed by performing PCR under the same conditions and was confirmed that the chloramphenicol marker was removed from the strain. The thus-constructed strain was named as "CJM2".

The CJM2 strain can accumulate an excessive amount of homoserine in the strain and can produce O-acetyl homoserine or O-succinylhomoserine according to the metX substrate specificity of the plasmid being introduced.

EXAMPLE 2

Selection of Polypeptides Having Novel O-Succinyltransferase Activity

For securing the release and stability of feedback control of metA gene, 10 types of orthologues named as metX in KEGG website (//www.genome.jp/kegg/) were selected and cloned into the pCL1920_PCJ1 vector. The CJM2 strain prepared in Example 1 was transformed with the 10 different types of vectors.

The thus-obtained 10 different kinds of strains were subjected to a flask evaluation using the flask culture method described in Example 5-(2) below. The CJM2 is a strain which can accumulate homoserine. When a homoserine succinyltransferase gene is introduced into the pCL1920, O-succinylhomoserine can be obtained as a final product, whereas when a homoserine acetyltransferase gene is introduced into the pCL1920, O-acetylhomoserine can be obtained as a final product. In this regard, a gene, which is a metX gene encoding homoserine succinyltransferase, was obtained among the 10 different types already evaluated. The gene is a *Chromobacterium Violaceum*-derived metX gene having the characteristic of producing O-succinylhomoserine with high yield (an amino acid sequence of SEQ ID NO: 29, and a nucleotide sequence of SEQ ID NO: 36), and the present inventors have confirmed that the above activity is a novel activity that has never been reported previously.

EXAMPLE 3

Plasmid Construction 3-1. Construction of a Plasmid Expressing metA Gene Derived from Wild-Type *E. coli*

PCR was performed using the chromosome of *E. coli* W3110 (Accession No: ATCC 9637) purchased from the American Type Culture Collection (ATCC) as a template, along with the primers of SEQ ID NO: 7 and SEQ ID NO: 8, to amplify the metA gene encoding homoserine O-succinyltransferase.

The primers used in the PCR were prepared based on the nucleotide sequence of *E. coli* chromosome (NC 000913) registered in the GenBank of the National Institutes of Health (NIH GenBank), and the primers of SEQ ID NO: 7 and SEQ ID NO: 8 have the EcoRV restriction site and the HindIII restriction site, respectively.

```
                                            <SEQ ID NO: 7>
5' AATTGATATCATGCCGATTCGTGTGCCGG 3'

<SEQ ID NO: 8>
5' AATTAAGCTTTTAATCCAGCGTTGGATTCATGTG 3'
```

The PCR was performed by denaturation at 94° C. for 3 min; 30 cycles of denaturation at 94° C. for 30 s, annealing at 56° C. for 30 s, and polymerization at 68° C. for 2 m; and polymerization at 68° C. for 10 m.

The pCL1920 plasmid including the thus-obtained PCR product and CJ1 promoter (Korean Pat. No. 0620092) was cloned after treating with EcoRV and HindIII, respectively. *E. coli* DH5α was transformed using the cloned plasmid and a plasmid was obtained by selecting the transformed *E. coli* DH5α from an LB plate containing spectinomycin (50 μg/mL). The thus-obtained plasmid was named as pCL_Pcj1_metA (wt).

3-2. Construction of a Plasmid Expressing metA Gene Having a Feedback-Resistance A metA gene (metA #11) having a feedback resistance to methionine was constructed using a site-directed mutagenesis kit; Stratagene, USA) based on the pCL_Pcj1_metA (wt) prepared in Example 3-1 as a template.

Specifically, according to the disclosure in International Patent Publication No. WO 2008/127240, the 29$^{th}$ amino acid, serine, was substituted with proline (S29P) using the primers of SEQ ID NO: 9 and SEQ ID NO: 10; the 114$^{th}$ amino acid, glutamic acid, was substituted with glycine (E114G) using the primers of SEQ ID NO: 11 and SEQ ID NO: 12; and the 140$^{th}$ amino acid, phenylalanine, was substituted with serine (F140S) using the primers of SEQ ID NO: 13 and SEQ ID NO: 14. The nucleotide sequences of the primers used are shown below.

```
                                            <SEQ ID NO: 9>
5' ATGACAACTTCTCGTGCGCCTGGTCAGGAAATTCG 3'

<SEQ ID NO: 10>
5' CGAATTTCCTGACCAGGCGCACGAGAAGTTGTCAT 3'

<SEQ ID NO: 11>
5' CGCCGCTGGGCCTGGTGGGGTTTAATGATGTCGCT 3'

<SEQ ID NO: 12>
5' AGCGACATCATTAAACCCCACCAGGCCCAGCGGCG 3'

<SEQ ID NO: 13>
5' CACGTCACCTCGACGCTGAGTGTCTGCTGGGCGGT 3'

<SEQ ID NO: 14>
5' ACCGCCCAGCAGACACTCAGCGTCGAGGTGACGTG 3'
```

A plasmid including the metA (#11) gene, which is introduced with all three kinds of the modifications by sequential introduction, was constructed and named as pCL_Pcj1_metA #11.

3-3. Construction of a Plasmid Expressing metX Gene Derived from *Deinococcus radiodurans*

PCR was performed using the chromosome of *Deinococcus radiodurans* (Accession No: ATCC BAA-816D) purchased from the American Type Culture Collection (ATCC) as a template, along with the primers of SEQ ID NO: 15 and SEQ ID NO: 16, to amplify the metX gene encoding homoserine 0-acetyl transferase.

The primers used in the PCR were prepared based on the nucleotide sequence of chromosome (AE000513) registered in the GenBank of the National Institutes of Health (NIH GenBank), and the primers of SEQ ID NO: 15 and SEQ ID NO: 16 have the EcoRV restriction site and the HindIII restriction site, respectively.

```
                                            <SEQ ID NO: 15>
5' AATTGATATCATGACCGCCGTGCTCGC 3'

<SEQ ID NO: 16>
5' AATTAAGCTTTCAACTCCTGAGAAACGCCCC 3'
```

The PCR was performed by denaturation at 94° C. for 3 min; 30 cycles of denaturation at 94° C. for 30 s, annealing at 56° C. for 30 s, and polymerization at 68° C. for 5 m; and polymerization at 68° C. for 7 m.

The pCL1920 plasmid including the thus-obtained PCR product and CJ1 promoter (Korean Pat. No. 0620092) was cloned after treating with EcoRV and HindIII, respectively. *E. coli* DH5α was transformed using the cloned plasmid and a plasmid was obtained by selecting the transformed *E. coli* DH5α from an LB plate containing spectinomycin (50 μg/mL). The thus-obtained plasmid was named as pCL_Pcj1_dra metX.

3-4. Construction of a Plasmid Expressing metX Gene Derived from *Chromobacterium Violaceum*

PCR was performed using the chromosome of *Chromobacterium Violaceum* (Accession No: ATCC 12472) purchased from the American Type Culture Collection (ATCC) as a template, along with the primers of SEQ ID NO: 17 and SEQ ID NO: 18, to amplify the metX gene derived from *Chromobacterium Violaceum*.

The primers used in the PCR were prepared based on the nucleotide sequence of *Chromobacterium Violaceum* chromosome (NC_005085) registered in the GenBank of the National Institutes of Health (NIH GenBank), and the primers of SEQ ID NO: 17 and SEQ ID NO: 18 have the EcoRV restriction site and the HindIII restriction site, respectively

```
                                      <SEQ ID NO: 17>
5' aatt gatatc ATGACCGACACCAACTGTTCGG 3'

<SEQ ID NO: 18>
5' aatt aagctt TCATGCGTTCACCTCCTTGGC 3'
```

The PCR was performed by denaturation at 94° C. for 3 min; 30 cycles of denaturation at 94° C. for 30 s, annealing at 56° C. for 30 s, and polymerization at 68° C. for 2 m; and polymerization at 68° C. for 10 m.

The pCL1920 plasmid including the thus-obtained PCR product and CJ1 promoter (Korean Pat. No. 0620092) was cloned after treating with EcoRV and HindIII, respectively. *E. coli* DH5α was transformed using the cloned plasmid and a plasmid was obtained by selecting the transformed *E. coli* DH5α from an LB plate containing spectinomycin (50 µg/mL). The thus-obtained plasmid was named as pCL_Pcj1_cvi metX.

3-5. A Plasmid for Construction of 2 Copy-Strain for Enhancing Biosynthesis Gene (1) Construction of pSG76c Vector for ppc Insertion In the present Example, pSG76c-2ppc, which is a vector for the insertion of *E. coli* chromosomal DNA including the ppc gene that encodes phosphoenolpyruvate carboxylase, was constructed.

The nucleotide sequence information of the ppc gene was obtained based on the NIH GenBank database (NCBI Reg. No. gi: 89110074), and the primers (SEQ ID NO: 19 and SEQ ID NO: 20), which include the ppc ORF, and EcoRI- and SacI restriction sites from the position −200 of the ppc gene, and the primers (SEQ ID NO: 21 and SEQ ID NO: 22), which include SacI- and KpnI restriction sites, were synthesized based on the information.

```
                                     <SEQ ID NO: 19>
5' gccggaattc tgtcggatgc gatacttgcg c 3'

<SEQ ID NO: 20>
5' gaaggagctc agaaaaccct cgcgcaaaag 3'

<SEQ ID NO: 21>
5' gccggagctc tgtcggatgc gatacttgcg c 3'

<SEQ ID NO: 22>
5' gaagggtacc agaaaaccct cgcgcaaaag 3'
```

PCR was performed using the chromosome of *E. coli* W3110 as a template along with the primers of SEQ ID NOS: 19 and 20 and SEQ ID NOS: 21 and 22. PfuUltra™ high-fidelity DNA polymerase (Stratagene) was used as polymerase, and the PCR was performed by denaturation at 94° C. for 3 min; 30 cycles of denaturation at 94° C. for 30 s, annealing at 56° C. for 30 s, and polymerization at 68° C. for 5 m; and polymerization at 68° C. for 7 m. As a result, the amplified ppc gene with a size of about 3.1 kb including EcoRI- and SacI restriction sites and the SacI- and KpnI restriction site was obtained.

After treating the end of the ppc gene obtained by PCR with EcoRI and SacI, and SacI and KpnI, the resulting ppc gene was ligated to the pSG76c vector (J Bacteriol. 1997 July; 179 (13): 4426-8), which was already treated with EcoRI and KpnI, and finally the pSG76c-2ppc recombinant vector into which two copies of the ppc gene are cloned, was constructed.

(2) Construction of pSG76c Vector for aspC Insertion

In the present Example, pSG76c-2aspC, which is a vector for the insertion of *E. coli* chromosomal DNA including the aspC gene that encodes aspartate aminotransferase, was constructed.

The nucleotide sequence information of the aspC gene was obtained based on the NIH GenBank database (NCBI Reg. No. gi: 85674274), and the primers (SEQ ID NO: 23 and SEQ ID NO: 24), which include the aspC ORF and SacI restriction site from the position −200 of the aspC gene, were synthesized based on the information.

```
                                     <SEQ ID NO: 23>
5' tccgagctca taagcgtagc gcatcaggca 3'

<SEQ ID NO: 24>
5' tccgagctcg tccacctatg ttgactacat 3'
```

PCR was performed using the chromosome of *E. coli* W3110 as a template along with the primers of oligonucleotides of SEQ ID NOS: 23 and 24. PfuUltra™ high-fidelity DNA polymerase (Stratagene) was used as polymerase, and the PCR was performed by denaturation at 94° C. for 3 min; 30 cycles of denaturation at 94° C. for 30 s, annealing at 56° C. for 30 s, and polymerization at 68° C. for 2 m; and polymerization at 68° C. for 7 m. As a result, the amplified aspC gene with a size of about 1.5 kb including BamHI restriction site was obtained.

After treating the end of the aspC gene obtained by PCR with BamHI, the resulting aspC gene was ligated to the pSG76c vector (J Bacteriol. 1997 July; 179 (13): 4426-8), which was already treated with BamHI, and finally the pSG76c-2aspC recombinant vector, into which two copies of the aspC gene are cloned, was constructed.

(3) Construction of pSG76c Vector for asd Insertion

In the present Example, pSG76c-2asd, which is a vector for the insertion of *E. coli* chromosomal DNA including the asd gene that encodes aspartate-semialdehyde dehydrogenase, was constructed.

The nucleotide sequence information of the asd gene was obtained based on the NIH GenBank database (NCBI Reg. No. gi: 89110578), and the primers (SEQ ID NO: 25 and SEQ ID NO: 26), which include the asd ORF, and EcoRI- and XbaI restriction sites from the position −200 of the asd gene, and the primers (SEQ ID NO: 27 and SEQ ID NO: 28), which include XbaI- and EcoRI restriction sites, were synthesized based on the information.

```
                                     <SEQ ID NO: 25>
5' ccggaattcc caggagagca ataagca 3'

<SEQ ID NO: 26>
5' ctagtctaga tgctctattt aactcccg 3'

<SEQ ID NO: 27>
5' ctagtctaga ccaggagagc aataagca 3'

<SEQ ID NO: 28>
5' ccggaattct gctctattta actcccg 3'
```

PCR was performed using the chromosome of *E. coli* W3110 as a template along with the primers of oligonucleotides of SEQ ID NOS: 25 and 26 and SEQ ID NOS: 27 and 28. PfuUltra™ high-fidelity DNA polymerase (Stratagene) was used as polymerase, and the PCR was performed for 30 cycles consisting of denaturation at 96° C. for 30 s, annealing at 50° C. for 30 s, and polymerization at 68° C. for 2 m. As a result, the amplified asd gene with a size of about 1.5 kb including EcoRI- and XbaI restriction sites and XbaI- and EcoRI restriction sites was obtained.

After treating the end of the asd gene obtained by PCR with EcoRI and XbaI, the resulting asd gene was ligated to the pSG76c vector, which was already treated with EcoRI, and finally the pSG76c-2asd recombinant vector, into which two copies of the asd gene are cloned, was constructed.

EXAMPLE 4

Construction of a Wild-Type Based Parent Strain (1) Enhancement of ppc, aspC, and asd Genes

*E. coli* W3110 (Accession No: ATCC 9637) purchased from the American Type Culture Collection (ATCC) was transformed with the pSG76c-2ppc, pSG76c-2aspC, pSG76c-2asd vectors prepared in Example 3-5, plated on LB-Cm (10 g/L of yeast extract, 5 g/L of NaCl, 10 g/L of tryptone, 25 μg/L of chloramphenicol, and 15 g/L of agar) plate medium, and the colonies which showed a resistance to chloramphenicol were selected. The selected transformants are the strains, in which the pSG76c-2ppc vector was firstly inserted into the ppc part of the genome.

The thus-obtained strain, in which 2 copies of the ppc gene are inserted, was transformed with the pST76-AsceP vector expressing I-SceI, which is a restriction enzyme digesting the I-SceI part present in the pSG76c vector, and plated on an LB-Ap (10 g/L of yeast extract, 5 g/L of NaCl, 10 g/L of tryptone, 100 μg/L of ampicillin, and 15 g/L of agar) plate medium, and the strains growing at 30° C. were selected.

The thus-grown strains may be in a state where the ppc gene was amplified to have 2 copies or may be returned to have a single copy. The strains with 2 copies of the ppc gene with an enlarged gene size of a 6.5 kb were selected in an 1% agarose gel electrophoresis after performing PCR using the primers of SEQ ID NO: 30 and SEQ ID NO: 31. As a result of the above process, the ppc gene becomes further inserted while the pSG76c vector is removed.

According to the method described above, the W3110 strains with amplified copies of ppc, asd, and aspC genes were constructed sequentially using the pSG76c-2aspC and pSG76c-2asd vectors. During the process, the construction of the strain with 2 copies of aspC gene was confirmed by identifying the gene with an enlarged size of 3.2 kb in an 1% agarose gel electrophoresis after performing PCR using the primers of SEQ ID NO: 32 and SEQ ID NO: 33, whereas the construction of the strain with 2 copies of asd gene was confirmed by identifying the gene with an enlarged size of 3.2 kb in an 1% agarose gel electrophoresis after performing PCR using the primers of SEQ ID NO: 34 and SEQ ID NO: 35. The thus constructed strain was named as CJW2.

```
                              <SEQ ID NO: 30>
CTGGCTCAATTAATCAGGCTC

<SEQ ID NO: 31>
CGAGGGTGTTAGAACAGAAGT

<SEQ ID NO: 32>
TGGTGAACTACTTTGAAGTGG

<SEQ ID NO: 33>
TGCGGCACGAGCGCCTTATCC

<SEQ ID NO: 34>
GCTCGTAGGCTAAGAAATGCC

<SEQ ID NO: 35>
CAGGTAAGGCTGTGAATACTC
```

(2) Deletion of metB, thrB, and metA Genes

The strain with deletion in metB, thrB, and metA genes was constructed in the same manner as in Example 3-1 using the CJW2 strain, and the strain was named as CJW2H. The CJW2H strain is a strain which can excessively accumulate homoserine within the strain and produce O-acetyl homoserine or O-succinylhomoserine depending on the metX substrate specificity of the plasmid being introduced.

EXAMPLE 5

Construction of Experimental Strains (1) Construction of Strains

The *E. coli* strains CJM2 and CJW2H constructed in Examples 1-(3) and 4-(2), respectively, were prepared into competent cells and introduced via electroporation with four different kinds of plasmids, pCL_Pcj1_metA (wt), pCL_Pcj1_metA #11, pCL_Pcj1_dra metX, and pCL_Pcj1_cvi metX, constructed in Examples 3-1, 3-2, 3-3, and 3-4, respectively.

(2) Flask Culture Experiment

Then, a flask test was performed to compare the kinds of the methionine precursors and the amount of production produced by each of the strains, which were introduced with the four kinds of plasmids, respectively. The flask test was performed as follows: each strain was streaked on an LB plate, cultured in a 31° C. incubator for 16 hours, and single colonies were inoculated into 3 mL of LB medium, and cultured in a 31° C. incubator at a rate of 200 rpm for 16 hours.

To a 250 mL flask was added 25 mL of a methionine precursor-producing medium shown in Table 1, and then added with 500 μL each of the culture broths prepared previously, respectively. Then, the flask was incubated in a 31° C. incubator at a rate of 200 rpm for 40 hours, and the kinds and amount of methionine precursors obtained in each of the strains introduced with each of the plasmids were compared. The results are shown in Tables 2 and 3 below.

TABLE 1

| Composition | Concentration (per Liter) |
|---|---|
| Glucose | 70 g |
| Ammonium sulfate | 25 g |
| $KH_2PO_4$ | 1 g |
| $MgSO_4 \cdot 7H_2O$ | 0.5 g |
| $FeSO_4 \cdot 7H_2O$ | 5 mg |
| $MnSO_4 \cdot 8H_2O$ | 5 mg |
| $ZnSO_4$ | 5 mg |
| Calcium carbonate | 30 g |
| Yeast extract | 2 g |
| Methionine | 0.3 g |
| Threonine | 1.5 g |

TABLE 2

| Strain | OD | Glucose consumption (g/L) | Product | Amount of product (g/L) |
|---|---|---|---|---|
| CJM2 pCL_Pcj1_metA (wt) | 18.8 | 58.2 | O-succinylhomoserine | 1.2 |
| CJM2 pCL_Pcj1_metA #11 | 18.5 | 68.0 | O-succinylhomoserine | 16.5 |
| CJM2 pCL_Pcj1_dra metX | 18.3 | 68.5 | O-acetylhomoserine | 13.0 |

TABLE 2-continued

| Strain | OD | Glucose consumption (g/L) | Product (g/L) | Amount of product (g/L) |
|---|---|---|---|---|
| CJM2 pCL_Pcj1_cvi metX | 18.5 | 67.8 | O-succinylhomoserine | 17.2 |

TABLE 3

| Strain | OD | Glucose consumption (g/L) | Product (g/L) | Amount of product (g/L) |
|---|---|---|---|---|
| CJW2H pCL_Pcj1_metA (wt) | 42.3 | 67.7 | O-succinylhomoserine | 0.9 |
| CJW2H pCL_Pcj1_metA #11 | 45.3 | 70.0 | O-succinylhomoserine | 6.5 |
| CJW2H pCL_Pcj1_dra metX | 44.2 | 70.0 | O-acetylhomoserine | 4.2 |
| CJW2H pCL_Pcj1_cvi metX | 43.8 | 70.0 | O-succinylhomoserine | 6.2 |

As a result, according to Tables 2 and 3, it was confirmed that CJM2 pCL_Pcj1_metA (wt), CJM2 pCL_Pcj1_metA#11, CJW2H pCL_Pcj1_metA (wt), and CJW2H pCL_Pcj1_metA #11 strains, which respectively includes *E. coli* wild type metA gene and metA#11 gene, which has a feedback resistance, produced O-succinylhomoserine, whereas CJM2 pCL_Pcj1_dra metX and CJW2H pCL_Pcj1_dra metX strains, which respectively includes metX gene derived from *Deinococcus radiodurans*, produced O-acetylhomoserine.

In the case of the metX gene derived from *Chromobacterium Violaceum*, the gene has high homology with other metX homologous genes (orthologues) compared to that of metA gene. However, regarding substrate specificity, the gene is homoserine succinyltransferase that produces succinylhomoserine, unlike the metX gene reported in general.

Additionally, in the case when the *E. coli* wild type metA(wt) gene was introduced, O-succinylhomoserine is produced about 1 g/L due to the phenomenon of feedback inhibition by methionine being added at a concentration of 0.3 g/L to the medium, whereas, in the case when metX gene derived from *Chromobacterium Violaceum* was introduced, O-succinylhomoserine was produced without the phenomenon of feedback inhibition by methionine added to the medium, even by the wild type itself without any introduction of gene modification.

The CJM2 strain introduced with pCL_Pcj1_cvi metX (CJM2 pCL_Pcj1_cvi metX) was deposited at the Korean Culture Center of Microorganisms (KCCM) located at 361-221, Hongje-1-dong, Seodaemun-gu, Seoul, Korea, which is a subsidiary of the Korean Federation of Culture Collections (KFCC), recognized as an international depositary authority under the Budapest Treaty, on Jun. 20, 2013 under the Accession Number KCCM11433P.

(3) Large Fermenter Culture Experiment

For large-scale production of O-succinylhomoserine, a methionine precursor, using CJM2 pCL_Pcj1_cvi metX and CJW2H pCL_Pcj1_cvi metX strains, a culture was performed in a 5 L fermenter.

An LB plate medium containing a spectinomycin antibiotic was inoculated with CJM2 pCL_Pcj1_cvi metX and CJW2H pCL_Pcj1_cvi metX strains and cultured at 31° C. overnight. Then, single colonies were inoculated into an 10 mL LB medium containing spectinomycin, cultured at 31° C. for 5 hours, and 2 mL of the culture was again inoculated into a 1000 mL Erlenmeyer flask containing 200 mL of a seed medium. Subsequently, the resultant was cultured in a 31° C. incubator at a rate of 200 rpm for 3 hours to 10 hours, and 255 mL of the seed culture was inoculated into 1.7 L of main medium of the 5 L fermenter to consume 1.3 L of the seed medium by fed batch method, and cultured for 50 hours to 100 hours.

The details of the medium components are shown in Table 4 below. The concentration of the thus-cultured fermentation liquid was analyzed via HPLC and the results are shown in Table 5 below.

TABLE 4

| Composition | Seed medium | Main medium | Feed medium |
|---|---|---|---|
| Glucose (g/L) | 10.1 | 40 | 560 |
| MgSO$_4$•7H$_2$O (g/L) | 0.5 | 4.2 | |
| Yeast extract (g/L) | 10 | 3.2 | |
| KH$_2$PO$_4$ | 3 | 3 | 8 |
| Ammonium sulfate (g/L) | | 6.3 | |
| NH$_4$Cl (g/L) | 1 | | |
| NaCl (g/L) | 0.5 | | |
| Na$_2$HPO$_4$•12H$_2$O (g/L) | 5.07 | | |
| DL-methionine (g/L) | | 0.5 | 0.5 |
| L-isoleucine (g/L) | 0.05 | 0.5 | 0.5 |
| L-threonine (g/L) | | 0.5 | 0.5 |

TABLE 5

| | Amount of O-succinylhomoserine production (g/L) |
|---|---|
| CJM2 pCL_Pcj1_cvi metX | 68 |
| CJW2H pCL_Pcj1_cvi metX | 18 |

As shown in Table 5 above, it was confirmed that the CJM2 pCL_Pcj1_cvi metX strain, in which the metX gene derived from *Chromobacterium Violaceum* was introduced based on the threonine-producing strain as the parent strain, accumulates O-succinylhomoserine at high level.

Those of ordinary skill in the art will recognize that the present invention may be embodied in other specific forms without departing from its spirit or essential characteristics. The described embodiments are to be considered in all respects only as illustrative and not restrictive. The scope of the present invention is, therefore, indicated by the appended claims rather than by the foregoing description. All changes which come within the meaning and range of equivalency of the claims are to be embraced within the scope of the present invention.

The invention claimed is:

1. An O-succinylhomoserine producing *Escherichia* sp. microorganism expressing a polypeptide, having a resistance to feedback inhibition by methionine and a homoserine O-succinyitransferase activity, wherein the polypeptide has an amino acid sequence represented by SEQ ID NO: 29, wherein the expression of said polypeptide results in increased production of O-succinylhomoserine compared to the same *Escherichia* sp. microorganism not expressing said polypeptide.

2. *Escherichia* sp. microorganism of claim 1, wherein the *Escherichia* sp. microorganism is *Escherichia coli*.

3. The *Escherichia* sp. microorganism of claim 1, wherein the metB gene encoding cystathionine gamma synthase is further deleted or weakened.

4. The *Escherichia* sp. microorganism of claim 1, wherein the thrB gene encoding homoserine kinase and the metA gene encoding homoserine O-succinyltransferase are further deleted or weakened.

5. The *Escherichia* sp. microorganism of claim 1, wherein phosphoenolpyruvate carboxylase, aspartate aminotransferase, and aspartate-semialdehyde dehydrogenase are further enhanced.

6. A method of producing O-succinylhomoserine, comprising:
   (a) culturing the microorganism of claim 1 in a medium; and
   (b) obtaining O-succinylhomoserine from the microorganism or the medium.

7. A method of producing O-succinylhomoserine, comprising:
   (a) culturing the microorganism of claim 2 in a medium; and
   (b) obtaining O-succinylhomoserine from the microorganism or the medium.

8. A method of producing O-succinylhomoserine, comprising:
   (a) culturing the microorganism of claim 3 in a medium; and
   (b) obtaining O-succinylhomoserine from the microorganism or the medium.

9. A method of producing O-succinylhomoserine, comprising:
   (a) culturing the microorganism of claim 4 in a medium; and
   (b) obtaining O-succinylhomoserine from the microorganism or the medium.

10. A method of producing O-succinylhomoserine, comprising:
    (a) culturing the microorganism of claim 5 in a medium; and
    (b) obtaining O-succinylhomoserine from the microorganism or the medium.

* * * * *

SEQUENCE LISTING

<160> NUMBER OF SEQ ID NOS: 36

<210> SEQ ID NO 1
<211> LENGTH: 70
<212> TYPE: DNA
<213> ORGANISM: Artificial Sequence
<220> FEATURE:
<223> OTHER INFORMATION: primer

<400> SEQUENCE: 1
ttactctggt gcctgacatt tcaccgacaa agcccaggga acttcatcac gtgtaggctg    60
gagctgcttc                                                          70

<210> SEQ ID NO 2
<211> LENGTH: 70
<212> TYPE: DNA
<213> ORGANISM: Artificial Sequence
<220> FEATURE:
<223> OTHER INFORMATION: primer

<400> SEQUENCE: 2 ttacccttg tttgcagccc ggaagccatt ttccaggtcg gcaattaaat catatgaata    60
tcctccttag                                                          70

<210> SEQ ID NO 3
<211> LENGTH: 70
<212> TYPE: DNA
<213> ORGANISM: Artificial Sequence
<220> FEATURE:
<223> OTHER INFORMATION: primer

<400> SEQUENCE: 3
aaagaatatg ccgatcggtt cgggcttagg ctccagtgcc tgttcggtgg gtgtaggctg    60
gagctgcttc                                                          70

<210> SEQ ID NO 4
<211> LENGTH: 70
<212> TYPE: DNA
<213> ORGANISM: Artificial Sequence
<220> FEATURE:
<223> OTHER INFORMATION: primer

<400> SEQUENCE: 4
agacaaccga catcgctttc aacattggcg accggagccg ggaaggcaaa catatgaata    60
tcctccttag                                                          70

<210> SEQ ID NO 5
<211> LENGTH: 70
<212> TYPE: DNA
<213> ORGANISM: Artificial Sequence
<220> FEATURE:
<223> OTHER INFORMATION: primer

<400> SEQUENCE: 5
caatttcttg cgtgaagaaa acgtctttgt gatgacaact tctcgtgcgt gtgtaggctg    60
gagctgcttc                                                          70

<210> SEQ ID NO 6
<211> LENGTH: 70
<212> TYPE: DNA
<213> ORGANISM: Artificial Sequence
<220> FEATURE:
<223> OTHER INFORMATION: primer

<400> SEQUENCE: 6
aatccagcgt tggattcatg tgccgtagat cgtatggcgt gatctggtag catatgaata    60
tcctccttag    70

<210> SEQ ID NO 7
<211> LENGTH: 29
<212> TYPE: DNA
<213> ORGANISM: Artificial Sequence
<220> FEATURE:
<223> OTHER INFORMATION: primer

<400> SEQUENCE: 7
aattgatatc atgccgattc gtgtgccgg    29

<210> SEQ ID NO 8
<211> LENGTH: 34
<212> TYPE: DNA
<213> ORGANISM: Artificial Sequence
<220> FEATURE:
<223> OTHER INFORMATION: primer

<400> SEQUENCE: 8
aattaagctt ttaatccagc gttggattca tgtg    34

<210> SEQ ID NO 9
<211> LENGTH: 35
<212> TYPE: DNA
<213> ORGANISM: Artificial Sequence
<220> FEATURE:
<223> OTHER INFORMATION: primer

<400> SEQUENCE: 9
atgacaactt ctcgtgcgcc tggtcaggaa attcg    35

<210> SEQ ID NO 10
<211> LENGTH: 35
<212> TYPE: DNA
<213> ORGANISM: Artificial Sequence
<220> FEATURE:
<223> OTHER INFORMATION: primer

<400> SEQUENCE: 10
cgaatttcct gaccaggcgc acgagaagtt gtcat    35

<210> SEQ ID NO 11
<211> LENGTH: 35
<212> TYPE: DNA
<213> ORGANISM: Artificial Sequence
<220> FEATURE:
<223> OTHER INFORMATION: primer

<400> SEQUENCE: 11
cgccgctggg cctggtgggg tttaatgatg tcgct    35

<210> SEQ ID NO 12
<211> LENGTH: 35
<212> TYPE: DNA
<213> ORGANISM: Artificial Sequence
<220> FEATURE:
<223> OTHER INFORMATION: primer

<400> SEQUENCE: 12
agcgacatca ttaaacccca ccaggcccag cggcg    35

<210> SEQ ID NO 13
<211> LENGTH: 35
<212> TYPE: DNA
<213> ORGANISM: Artificial Sequence
<220> FEATURE:
<223> OTHER INFORMATION: primer

<400> SEQUENCE: 13
cacgtcacct cgacgctgag tgtctgctgg gcggt                               35

<210> SEQ ID NO 14
<211> LENGTH: 35
<212> TYPE: DNA
<213> ORGANISM: Artificial Sequence
<220> FEATURE:
<223> OTHER INFORMATION: primer

<400> SEQUENCE: 14
accgcccagc agacactcag cgtcgaggtg acgtg                               35

<210> SEQ ID NO 15
<211> LENGTH: 27
<212> TYPE: DNA
<213> ORGANISM: Artificial Sequence
<220> FEATURE:
<223> OTHER INFORMATION: primer

<400> SEQUENCE: 15
aattgatatc atgaccgccg tgctcgc                                        27

<210> SEQ ID NO 16
<211> LENGTH: 31
<212> TYPE: DNA
<213> ORGANISM: Artificial Sequence
<220> FEATURE:
<223> OTHER INFORMATION: primer

<400> SEQUENCE: 16
aattaagctt tcaactcctg agaaacgccc c                                   31

<210> SEQ ID NO 17
<211> LENGTH: 32
<212> TYPE: DNA
<213> ORGANISM: Artificial Sequence
<220> FEATURE:
<223> OTHER INFORMATION: primer

<400> SEQUENCE: 17
aattgatatc atgaccgaca ccaactgttc gg                                  32

<210> SEQ ID NO 18
<211> LENGTH: 31
<212> TYPE: DNA
<213> ORGANISM: Artificial Sequence
<220> FEATURE:
<223> OTHER INFORMATION: primer

<400> SEQUENCE: 18
aattaagctt tcatgcgttc acctccttgg c                                   31

<210> SEQ ID NO 19
<211> LENGTH: 31
<212> TYPE: DNA
<213> ORGANISM: Artificial Sequence
<220> FEATURE:
<223> OTHER INFORMATION: primer

```
<400> SEQUENCE: 19
gccggaattc tgtcggatgc gatacttgcg c                              31

<210> SEQ ID NO 20
<211> LENGTH: 30
<212> TYPE: DNA
<213> ORGANISM: Artificial Sequence
<220> FEATURE:
<223> OTHER INFORMATION: primer

<400> SEQUENCE: 20
gaaggagctc agaaaaccct cgcgcaaaag                                30

<210> SEQ ID NO 21
<211> LENGTH: 31
<212> TYPE: DNA
<213> ORGANISM: Artificial Sequence
<220> FEATURE:
<223> OTHER INFORMATION: primer

<400> SEQUENCE: 21
gccggagctc tgtcggatgc gatacttgcg c                              31

<210> SEQ ID NO 22
<211> LENGTH: 30
<212> TYPE: DNA
<213> ORGANISM: Artificial Sequence
<220> FEATURE:
<223> OTHER INFORMATION: primer

<400> SEQUENCE: 22
gaagggtacc agaaaaccct cgcgcaaaag                                30

<210> SEQ ID NO 23
<211> LENGTH: 30
<212> TYPE: DNA
<213> ORGANISM: Artificial Sequence
<220> FEATURE:
<223> OTHER INFORMATION: primer

<400> SEQUENCE: 23
tccgagctca taagcgtagc gcatcaggca                                30

<210> SEQ ID NO 24
<211> LENGTH: 30
<212> TYPE: DNA
<213> ORGANISM: Artificial Sequence
<220> FEATURE:
<223> OTHER INFORMATION: primer

<400> SEQUENCE: 24
tccgagctcg tccacctatg ttgactacat                                30

<210> SEQ ID NO 25
<211> LENGTH: 27
<212> TYPE: DNA
<213> ORGANISM: Artificial Sequence
<220> FEATURE:
<223> OTHER INFORMATION: primer

<400> SEQUENCE: 25
ccggaattcc caggagagca ataagca                                   27

<210> SEQ ID NO 26
```

```
<211> LENGTH: 28
<212> TYPE: DNA
<213> ORGANISM: Artificial Sequence
<220> FEATURE:
<223> OTHER INFORMATION: primer

<400> SEQUENCE: 26
ctagtctaga tgctctattt aactcccg                                         28

<210> SEQ ID NO 27
<211> LENGTH: 28
<212> TYPE: DNA
<213> ORGANISM: Artificial Sequence
<220> FEATURE:
<223> OTHER INFORMATION: primer

<400> SEQUENCE: 27
ctagtctaga ccaggagagc aataagca                                         28

<210> SEQ ID NO 28
<211> LENGTH: 27
<212> TYPE: DNA
<213> ORGANISM: Artificial Sequence
<220> FEATURE:
<223> OTHER INFORMATION: primer

<400> SEQUENCE: 28
ccggaattct gctctattta actcccg                                          27

<210> SEQ ID NO 29
<211> LENGTH: 380
<212> TYPE: PRT
<213> ORGANISM: Chromobacterium Violaceum
<220> FEATURE:
<221> NAME/KEY: PEPTIDE
<222> LOCATION: (1)..(380)
<223> OTHER INFORMATION: homoserine O-succinyltransferase

<400> SEQUENCE: 29
```

Met Thr Asp Thr Asn Cys Ser Val Gly Ile Val Ala Ala Gln Asp Ala
1               5                   10                  15

Ala Phe Asp Ile Pro Leu Pro Leu Ala Ser Gly Ala Ala Leu Pro Gly
            20                  25                  30

Tyr Gln Leu Arg Phe Glu Thr Tyr Gly Lys Leu Asn Ala Asp Lys Ser
        35                  40                  45

Asn Ala Ile Leu Ile Cys His Ala Leu Ser Gly His His Val Ala
    50                  55                  60

Gly Tyr Tyr Arg Ala Asp Asp Lys Thr Pro Gly Trp Trp Asp Asn Met
65                  70                  75                  80

Ile Gly Pro Gly Lys Pro Ile Asp Thr Arg Arg Phe Phe Val Val Gly
                85                  90                  95

Val Asn Asn Leu Gly Gly Cys His Gly Ser Thr Gly Pro Ser Ser Val
            100                 105                 110

Asn Pro Ala Thr Gly Gln Pro Trp Gly Ser Ala Phe Pro Val Met Thr
        115                 120                 125

Val Pro Asp Trp Val Thr Ser Gln Ala Arg Leu Ala Asp Arg Leu Gly
    130                 135                 140

Ile Glu Arg Trp Ala Ala Val Ile Gly Gly Ser Leu Gly Gly Met Gln
145                 150                 155                 160

Ala Leu His Trp Ser Ile Ala Tyr Pro Glu Arg Val Ala His Ala Leu
                165                 170                 175

Val Ile Ala Ser Ala Pro Lys Leu Ser Ala Gln Asn Ile Ala Phe Asn
            180                 185                 190

Asp Val Ala Arg Gln Ala Ile Leu Thr Asp Pro Asp Phe Cys Gly Gly
        195                 200                 205

Asp Phe Tyr Gln Gln Gly Thr Ile Pro Arg Arg Gly Leu Arg Leu Ala
    210                 215                 220

Arg Met Leu Gly His Ile Thr Tyr Leu Ser Asp Gly Met Gly Glu
225                 230                 235                 240

Lys Phe Gly Arg Met Leu Arg Ser Gly Glu Tyr Arg Phe Gly Tyr Asp
                245                 250                 255

Val Glu Phe Glu Ile Glu Ser Tyr Leu Arg Tyr Gln Gly Asp Lys Phe
            260                 265                 270

Ser Asp Tyr Phe Asp Ala Asn Thr Tyr Leu Leu Met Thr Lys Ala Leu
        275                 280                 285

Asp Tyr Phe Asp Pro Ala Ala Ala His Gly Gly Asp Leu Ala Ala Ala
    290                 295                 300

Leu Lys Pro Ala Gln Ala Ala Phe Met Val Ala Ser Phe Thr Ser Asp
305                 310                 315                 320

Trp Arg Phe Ser Pro Glu Arg Ser Arg Glu Thr Val Lys Ala Leu Ile
                325                 330                 335

Ala Ala Gly Lys Arg Val Ser Tyr Ala Glu Ile Glu Ser Val His Gly
            340                 345                 350

His Asp Ala Phe Leu Met Thr Asp Gln Pro Tyr Val Asp Leu Met Arg
        355                 360                 365

Ala Tyr Leu Asp Arg Val Ala Lys Glu Val Asn Ala
    370                 375                 380

<210> SEQ ID NO 30
<211> LENGTH: 21
<212> TYPE: DNA
<213> ORGANISM: Artificial Sequence
<220> FEATURE:
<223> OTHER INFORMATION: primer

<400> SEQUENCE: 30
ctggctcaat taatcaggct c                                         21

<210> SEQ ID NO 31
<211> LENGTH: 21
<212> TYPE: DNA
<213> ORGANISM: Artificial Sequence
<220> FEATURE:
<223> OTHER INFORMATION: primer

<400> SEQUENCE: 31
cgagggtgtt agaacagaag t                                         21

<210> SEQ ID NO 32
<211> LENGTH: 21
<212> TYPE: DNA
<213> ORGANISM: Artificial Sequence
<220> FEATURE:
<223> OTHER INFORMATION: primer

<400> SEQUENCE: 32
tggtgaacta ctttgaagtg g                                         21

<210> SEQ ID NO 33
<211> LENGTH: 21
<212> TYPE: DNA

<213> ORGANISM: Artificial Sequence
<220> FEATURE:
<223> OTHER INFORMATION: primer

<400> SEQUENCE: 33
tgcggcacga gcgccttatc c                                              21

<210> SEQ ID NO 34
<211> LENGTH: 21
<212> TYPE: DNA
<213> ORGANISM: Artificial Sequence
<220> FEATURE:
<223> OTHER INFORMATION: primer

<400> SEQUENCE: 34
gctcgtaggc taagaaatgc c                                              21

<210> SEQ ID NO 35
<211> LENGTH: 21
<212> TYPE: DNA
<213> ORGANISM: Artificial Sequence
<220> FEATURE:
<223> OTHER INFORMATION: primer

<400> SEQUENCE: 35
caggtaaggc tgtgaatact c                                              21

<210> SEQ ID NO 36
<211> LENGTH: 1143
<212> TYPE: DNA
<213> ORGANISM: Chromobacterium Violaceum

<400> SEQUENCE: 36
atgaccgaca ccaactgttc ggtaggcatc gtcgcggccc aggatgccgc gttcgacatt      60
cccctgccgc tcgccagcgg cgccgcgctg ccgggctatc agctgcgttt cgagacctac     120
ggcaaactca acgccgacaa gagcaacgcc atcctgatct gccacgcatt gtccggccac     180
caccatgtcg ccggctatta ccgcgccgac gacaagaccc cgggctggtg gacaatatg     240
atcggcccg gcaagccgat cgacacccgc cgcttcttcg tggtcggcgt caacaacctg     300
ggcggttgcc acggcagcac cggcccgtcc agcgtcaacc cggccaccgg ccagccgtgg     360
ggctcggcct ttccggtgat gacggtgccg gactgggtga cctcgcaggc gcgcctggcc     420
gaccggctcg gcattgaacg ctgggcggcg gtgataggcg gctcgctggg cggcatgcag     480
gcgctgcact ggagcatcgc ctatccggaa cgcgtcgcgc acgcgctggt gatcgcctcc     540
gcgcccaagc tgtcggcgca gaacatcgcc ttcaacgacg tcgcgcgcca ggccatcctc     600
accgacccgg acttttgcgg cggcgacttc taccagcagg gcaccatccc ccgccgcggc     660
ctcaggctgg cgcggatgct gggccacatc acctatctgt ccgacgatgg catgggcgag     720
aaattcggcc gcatgctgcg ctcgggggaa taccgcttcg gctacgacgt ggagttcgag     780
atcgagagct acctgcgcta ccaaggcgac aagttctccg attacttcga cgccaacacc     840
tatctgctga tgaccaaggc gctggactac ttcgaccccg ccgccgcgca cggcggcgac     900
ctggccgccg cgctgaagcc ggcgcaggcg cgttcatgg tggccagctt caccagcgac     960
tggcgcttct cgccggagcg ctcgcgcgag acggtgaagg cgctgatcgc cgccggcaag    1020

```
cgcgtcagct acgccgagat cgagtcggtg cacggccacg acgccttcct gatgaccgac    1080
caaccgtatg tggacctgat gcgcgcctac ctggaccgcg tggccaagga ggtgaacgca    1140
tga                                                                  1143
```